(12) United States Patent
Jafari et al.

(10) Patent No.: US 8,272,380 B2
(45) Date of Patent: Sep. 25, 2012

(54) LEAK-COMPENSATED PRESSURE TRIGGERING IN MEDICAL VENTILATORS

(75) Inventors: Mehdi M. Jafari, Laguna Hills, CA (US); Jeffrey K. Aviano, Escondido, CA (US); Rhomere S. Jimenez, Winchester, CA (US); Gail F. Upham, Fallbrook, CA (US)

(73) Assignee: Nellcor Puritan Bennett, LLC, Boulder, CO (US)

( * ) Notice: Subject to any disclaimer, the term of this patent is extended or adjusted under 35 U.S.C. 154(b) by 929 days.

(21) Appl. No.: 12/242,756

(22) Filed: Sep. 30, 2008

(65) Prior Publication Data
US 2009/0241951 A1    Oct. 1, 2009

Related U.S. Application Data
(60) Provisional application No. 61/041,070, filed on Mar. 31, 2008.

(51) Int. Cl.
*A61M 11/00* (2006.01)
(52) U.S. Cl. .................................. 128/204.21
(58) Field of Classification Search ............ 128/202.22, 128/204.18, 204.21, 204.23, 204.26, 848, 128/205.25, 207.18
See application file for complete search history.

(56) References Cited

U.S. PATENT DOCUMENTS

| | | | |
|---|---|---|---|
| 3,805,780 A | 4/1974 | Cramer et al. |
| 3,941,124 A | 3/1976 | Rodewald et al. |
| 4,056,098 A | 11/1977 | Michel et al. |
| 4,305,388 A | 12/1981 | Brisson |
| 4,340,044 A | 7/1982 | Levy et al. |
| 4,766,894 A | 8/1988 | Legrand et al. |
| 4,939,647 A | 7/1990 | Clough et al. |
| 4,971,052 A | 11/1990 | Edwards |
| 4,972,842 A | 11/1990 | Korten et al. |
| 4,986,268 A | 1/1991 | Tehrani |
| 5,072,728 A | 12/1991 | Pasternack |
| 5,094,235 A | 3/1992 | Westenskow et al. |
| 5,148,802 A | 9/1992 | Sanders et al. |
| 5,239,995 A | 8/1993 | Estes et al. |
| 5,259,373 A | 11/1993 | Gruenke et al. |
| 5,313,937 A | 5/1994 | Zdrojkowski et al. |

(Continued)

FOREIGN PATENT DOCUMENTS
DE    19808543 A1    11/1998
(Continued)

OTHER PUBLICATIONS

PCT International Search Report and Written Opinion in Application PCT/US2010/025485, mailed Feb. 27, 2009, 8 pgs.

(Continued)

*Primary Examiner* — Steven Douglas
(74) *Attorney, Agent, or Firm* — Merchant & Gould PC (57) ABSTRACT

This disclosure describes systems and methods for compensating for inelastic and elastic leaks in a ventilation system. The disclosure describes a model-based enhancement to conventional pressure triggering methodology that optimizes the timing and patient work of pressure triggering performance. The methods and systems described herein compensate for the additional effort a patient has to exert to generate the same amount of airway pressure drops compared to no leak condition. One method described includes calculating an elastic leakage and an inelastic leakage based on current measurements of pressure and flow in the ventilation system and then compensating a pressure threshold for the effects of the inelastic and elastic leaks in the system.

23 Claims, 3 Drawing Sheets

U.S. PATENT DOCUMENTS

| | | | |
|---|---|---|---|
| 5,315,989 A | 5/1994 | Tobia |
| 5,316,009 A | 5/1994 | Yamada |
| 5,365,922 A | 11/1994 | Raemer |
| 5,388,575 A | 2/1995 | Taube |
| 5,398,682 A | 3/1995 | Lynn |
| 5,429,123 A | 7/1995 | Shaffer et al. |
| 5,433,193 A | 7/1995 | Sanders et al. |
| 5,492,113 A | 2/1996 | Estes et al. |
| 5,503,146 A | 4/1996 | Froehlich et al. |
| 5,503,147 A | 4/1996 | Bertheau |
| 5,535,738 A | 7/1996 | Estes et al. |
| 5,540,220 A | 7/1996 | Gropper et al. |
| 5,551,418 A | 9/1996 | Estes et al. |
| 5,551,419 A | 9/1996 | Froehlich et al. |
| 5,555,880 A | 9/1996 | Winter et al. |
| 5,598,838 A | 2/1997 | Servidio et al. |
| 5,605,151 A | 2/1997 | Lynn |
| 5,623,923 A | 4/1997 | Bertheau et al. |
| 5,632,269 A | 5/1997 | Zdrojkowski |
| 5,645,053 A | 7/1997 | Remmers et al. |
| 5,664,562 A | 9/1997 | Bourdon |
| 5,685,296 A | 11/1997 | Zdrojkowski et al. |
| 5,687,715 A | 11/1997 | Landis et al. |
| 5,692,497 A | 12/1997 | Schnitzer et al. |
| 5,752,509 A | 5/1998 | Lachmann et al. |
| 5,794,615 A | 8/1998 | Estes |
| 5,803,065 A * | 9/1998 | Zdrojkowski et al. ... 128/204.23 |
| 5,823,187 A | 10/1998 | Estes et al. |
| 5,884,622 A | 3/1999 | Younes |
| 5,891,023 A | 4/1999 | Lynn |
| 5,901,704 A | 5/1999 | Estes et al. |
| 5,904,141 A | 5/1999 | Estes et al. |
| 5,921,920 A | 7/1999 | Marshall et al. |
| 5,927,274 A | 7/1999 | Servidio et al. |
| 5,970,975 A | 10/1999 | Estes et al. |
| 6,029,664 A | 2/2000 | Zdrojkowski et al. |
| 6,055,981 A | 5/2000 | Laswick et al. |
| 6,105,575 A | 8/2000 | Estes et al. |
| 6,123,074 A | 9/2000 | Hete et al. |
| 6,148,814 A | 11/2000 | Clemmer et al. |
| 6,152,129 A | 11/2000 | Berthon-Jones |
| 6,158,432 A | 12/2000 | Biondi et al. |
| 6,223,064 B1 | 4/2001 | Lynn et al. |
| 6,253,765 B1 | 7/2001 | Högnelid et al. |
| 6,257,234 B1 | 7/2001 | Sun |
| 6,279,569 B1 | 8/2001 | Berthon-Jones |
| 6,286,508 B1 | 9/2001 | Remmers et al. |
| 6,305,372 B1 | 10/2001 | Servidio |
| 6,305,374 B1 | 10/2001 | Zdrojkowski et al. |
| 6,321,748 B1 | 11/2001 | O'Mahoney |
| 6,342,039 B1 | 1/2002 | Lynn et al. |
| 6,360,741 B2 | 3/2002 | Truschel |
| 6,371,114 B1 | 4/2002 | Schmidt et al. |
| 6,390,091 B1 | 5/2002 | Banner et al. |
| 6,425,395 B1 | 7/2002 | Brewer et al. |
| 6,427,689 B1 | 8/2002 | Estes et al. |
| 6,484,719 B1 | 11/2002 | Berthon-Jones |
| 6,512,938 B2 | 1/2003 | Claure et al. |
| 6,532,957 B2 | 3/2003 | Berthon-Jones |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |
| 6,536,432 B2 | 3/2003 | Truschel |
| 6,539,940 B2 | 4/2003 | Zdrojkowski et al. |
| 6,543,449 B1 | 4/2003 | Woodring et al. |
| 6,550,478 B2 | 4/2003 | Remmers et al. |
| 6,553,992 B1 | 4/2003 | Berthon-Jones et al. |
| 6,561,187 B2 | 5/2003 | Schmidt et al. |
| 6,575,163 B1 | 6/2003 | Berthon-Jones |
| 6,578,575 B1 | 6/2003 | Jonson |
| 6,609,016 B1 | 8/2003 | Lynn |
| 6,609,517 B1 | 8/2003 | Estes et al. |
| 6,615,834 B2 | 9/2003 | Gradon et al. |
| 6,626,175 B2 | 9/2003 | Jafari et al. |
| 6,629,527 B1 | 10/2003 | Estes et al. |
| 6,640,806 B2 | 11/2003 | Yurko |
| 6,644,312 B2 | 11/2003 | Berthon-Jones et al. |
| 6,644,316 B2 | 11/2003 | Bowman et al. |
| 6,659,101 B2 | 12/2003 | Berthon-Jones |
| 6,671,529 B2 | 12/2003 | Claure et al. |
| 6,688,307 B2 | 2/2004 | Berthon-Jones |
| 6,701,926 B2 | 3/2004 | Olsen et al. |
| 6,722,365 B2 | 4/2004 | Nilsson et al. |
| 6,723,055 B2 | 4/2004 | Hoffman |
| 6,723,132 B2 | 4/2004 | Salehpoor |
| 6,748,252 B2 | 6/2004 | Lynn et al. |
| 6,752,150 B1 | 6/2004 | Remmers et al. |
| 6,752,151 B2 | 6/2004 | Hill |
| 6,755,193 B2 | 6/2004 | Berthon-Jones et al. |
| 6,758,216 B1 | 7/2004 | Berthon-Jones et al. |
| 6,760,608 B2 | 7/2004 | Lynn |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,789,541 B2 | 9/2004 | Olsen et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,618 B2 | 11/2004 | Banner et al. |
| 6,823,866 B2 | 11/2004 | Jafari et al. |
| 6,837,242 B2 | 1/2005 | Younes |
| 6,843,250 B2 | 1/2005 | Efrati |
| 6,868,346 B2 | 3/2005 | Larson et al. |
| 6,874,503 B2 | 4/2005 | Rydgren |
| 6,910,480 B1 | 6/2005 | Berthon-Jones |
| 6,910,481 B2 | 6/2005 | Kimmel et al. |
| 6,920,875 B1 | 7/2005 | Hill et al. |
| 6,920,877 B2 | 7/2005 | Remmers et al. |
| 6,932,084 B2 | 8/2005 | Estes et al. |
| 6,945,248 B2 | 9/2005 | Berthon-Jones |
| 6,948,497 B2 | 9/2005 | Zdrojkowski et al. |
| 6,962,155 B1 | 11/2005 | Sinderby |
| 6,986,347 B2 | 1/2006 | Hickle |
| 7,000,612 B2 | 2/2006 | Jafari et al. |
| 7,008,380 B1 | 3/2006 | Rees et al. |
| 7,013,892 B2 | 3/2006 | Estes et al. |
| 7,017,576 B2 | 3/2006 | Olsen et al. |
| 7,040,320 B2 | 5/2006 | Fjeld et al. |
| 7,055,522 B2 | 6/2006 | Berthon-Jones |
| 7,066,173 B2 | 6/2006 | Banner et al. |
| 7,073,501 B2 | 7/2006 | Remmers et al. |
| 7,081,095 B2 | 7/2006 | Lynn et al. |
| 7,089,936 B2 | 8/2006 | Madaus et al. |
| 7,092,757 B2 | 8/2006 | Larson et al. |
| 7,100,607 B2 | 9/2006 | Zdrojkowski et al. |
| 7,100,608 B2 | 9/2006 | Brewer et al. |
| 7,100,609 B2 | 9/2006 | Berthon-Jones et al. |
| 7,107,991 B2 | 9/2006 | Kolobow |
| 7,137,389 B2 | 11/2006 | Berthon-Jones |
| 7,152,598 B2 | 12/2006 | Morris et al. |
| 7,168,429 B2 | 1/2007 | Matthews et al. |
| 7,195,028 B2 | 3/2007 | Basset et al. |
| 7,210,478 B2 | 5/2007 | Banner et al. |
| 7,229,430 B2 | 6/2007 | Hickle et al. |
| 7,267,122 B2 | 9/2007 | Hill |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,331,343 B2 | 2/2008 | Schmidt et al. |
| 7,353,824 B1 | 4/2008 | Forsyth et al. |
| 7,367,337 B2 | 5/2008 | Berthon-Jones et al. |
| 7,370,650 B2 | 5/2008 | Nadjafizadeh et al. |
| 7,398,115 B2 | 7/2008 | Lynn |
| 7,406,870 B2 | 8/2008 | Seto |
| 7,448,381 B2 | 11/2008 | Sasaki et al. |
| 7,455,583 B2 | 11/2008 | Taya et al. |
| 7,475,685 B2 | 1/2009 | Dietz et al. |
| 7,509,957 B2 | 3/2009 | Duquette et al. |
| 7,527,056 B2 | 5/2009 | Turiello |
| 7,533,671 B2 | 5/2009 | Gonzalez et al. |
| 7,621,269 B2 | 11/2009 | Turiello |
| 7,644,713 B2 | 1/2010 | Berthon-Jones |
| 7,661,428 B2 | 2/2010 | Berthon-Jones |
| 7,673,629 B2 | 3/2010 | Turiello |
| 7,677,247 B2 | 3/2010 | Turiello |
| 7,694,678 B2 | 4/2010 | Turiello |

| Patent/Publication No. | Date | Name |
|---|---|---|
| 7,717,112 B2 | 5/2010 | Sun et al. |
| 7,770,578 B2 | 8/2010 | Estes et al. |
| 7,810,496 B2 | 10/2010 | Estes et al. |
| 7,810,497 B2 | 10/2010 | Pittman et al. |
| 7,814,906 B2 | 10/2010 | Moretti |
| 7,827,988 B2 | 11/2010 | Matthews et al. |
| 7,856,979 B2 | 12/2010 | Doshi et al. |
| 7,882,835 B2 | 2/2011 | Eger et al. |
| 7,886,739 B2 | 2/2011 | Soliman et al. |
| 7,886,740 B2 | 2/2011 | Thomas et al. |
| 7,905,231 B2 | 3/2011 | Chalvignac |
| 7,918,222 B2 | 4/2011 | Chen |
| 7,918,223 B2 | 4/2011 | Soliman et al. |
| 7,920,067 B2 | 4/2011 | Durtschi et al. |
| 7,928,852 B2 | 4/2011 | Durtschi et al. |
| 7,934,499 B2 | 5/2011 | Berthon-Jones |
| 7,938,114 B2 | 5/2011 | Matthews et al. |
| 7,963,283 B2 | 6/2011 | Sinderby |
| 7,984,712 B2 | 7/2011 | Soliman et al. |
| 8,002,154 B2 | 8/2011 | Fontela et al. |
| 8,021,309 B2 | 9/2011 | Zilberg |
| 8,033,280 B2 | 10/2011 | Heinonen |
| 2002/0014240 A1 | 2/2002 | Truschel |
| 2002/0053345 A1 | 5/2002 | Jafari et al. |
| 2002/0185126 A1 | 12/2002 | Krebs |
| 2003/0158466 A1 | 8/2003 | Lynn et al. |
| 2003/0221689 A1 | 12/2003 | Berthon-Jones |
| 2004/0074492 A1 | 4/2004 | Berthon-Jones |
| 2004/0089561 A1 | 5/2004 | Herman |
| 2004/0163648 A1 | 8/2004 | Burton |
| 2004/0187870 A1 | 9/2004 | Matthews et al. |
| 2005/0109340 A1 | 5/2005 | Tehrani |
| 2005/0172965 A1 | 8/2005 | Thulin |
| 2005/0188991 A1 | 9/2005 | Sun et al. |
| 2005/0241639 A1 | 11/2005 | Zilberg |
| 2006/0000475 A1 | 1/2006 | Matthews et al. |
| 2006/0011200 A1 | 1/2006 | Remmers et al. |
| 2006/0086357 A1 | 4/2006 | Soliman et al. |
| 2006/0102180 A1 | 5/2006 | Berthon-Jones |
| 2006/0112959 A1 | 6/2006 | Mechlenburg et al. |
| 2006/0118112 A1 | 6/2006 | Cattano et al. |
| 2006/0144144 A1 | 7/2006 | Seto |
| 2006/0150974 A1 | 7/2006 | Berthon-Jones |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0174883 A1 | 8/2006 | Aylsworth et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0217633 A1 | 9/2006 | Glocker et al. |
| 2006/0235324 A1 | 10/2006 | Lynn |
| 2006/0241708 A1 | 10/2006 | Boute |
| 2006/0247508 A1 | 11/2006 | Fennell |
| 2006/0249150 A1 | 11/2006 | Dietz et al. |
| 2006/0249156 A1 | 11/2006 | Moretti |
| 2006/0254588 A1 | 11/2006 | Brewer et al. |
| 2006/0264762 A1 | 11/2006 | Starr |
| 2006/0272642 A1 | 12/2006 | Chalvignac |
| 2006/0278218 A1 | 12/2006 | Hoffman |
| 2007/0000494 A1 | 1/2007 | Banner et al. |
| 2007/0027375 A1 | 2/2007 | Melker et al. |
| 2007/0028921 A1 | 2/2007 | Banner et al. |
| 2007/0044796 A1 | 3/2007 | Zdrojkowski et al. |
| 2007/0068530 A1 | 3/2007 | Pacey |
| 2007/0072541 A1 | 3/2007 | Daniels, II et al. |
| 2007/0077200 A1 | 4/2007 | Baker |
| 2007/0089738 A1 | 4/2007 | Soliman et al. |
| 2007/0093721 A1 | 4/2007 | Lynn et al. |
| 2007/0101992 A1 | 5/2007 | Soliman et al. |
| 2007/0129647 A1 | 6/2007 | Lynn |
| 2007/0135736 A1 | 6/2007 | Addington et al. |
| 2007/0144522 A1 | 6/2007 | Eger et al. |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0221224 A1 | 9/2007 | Pittman et al. |
| 2007/0251532 A1 | 11/2007 | Friedberg |
| 2007/0272241 A1 | 11/2007 | Sanborn et al. |
| 2007/0277823 A1 | 12/2007 | Al-Ali et al. |
| 2007/0283958 A1 | 12/2007 | Naghavi |
| 2008/0000478 A1 | 1/2008 | Matthiessen et al. |
| 2008/0000479 A1 | 1/2008 | Elaz et al. |
| 2008/0041382 A1 | 2/2008 | Matthews et al. |
| 2008/0041383 A1 | 2/2008 | Matthews et al. |
| 2008/0051674 A1 | 2/2008 | Davenport et al. |
| 2008/0053442 A1 | 3/2008 | Estes et al. |
| 2008/0053443 A1 | 3/2008 | Estes et al. |
| 2008/0053444 A1 | 3/2008 | Estes et al. |
| 2008/0066752 A1 | 3/2008 | Baker et al. |
| 2008/0066753 A1 | 3/2008 | Martin et al. |
| 2008/0081974 A1 | 4/2008 | Pav |
| 2008/0097234 A1 | 4/2008 | Nicolazzi et al. |
| 2008/0168988 A1 | 7/2008 | Lu |
| 2008/0178880 A1 | 7/2008 | Christopher et al. |
| 2008/0178882 A1 | 7/2008 | Christopher et al. |
| 2008/0185002 A1 | 8/2008 | Berthon-Jones et al. |
| 2008/0200775 A1 | 8/2008 | Lynn |
| 2008/0200819 A1 | 8/2008 | Lynn et al. |
| 2008/0221469 A1 | 9/2008 | Shevchuk |
| 2008/0251079 A1 | 10/2008 | Richey |
| 2008/0295837 A1 | 12/2008 | McCormick et al. |
| 2008/0302359 A1 | 12/2008 | Loomas et al. |
| 2009/0014007 A1 | 1/2009 | Brambilla et al. |
| 2009/0050153 A1 | 2/2009 | Brunner |
| 2009/0082653 A1 | 3/2009 | Rohde |
| 2009/0088613 A1 | 4/2009 | Marttila et al. |
| 2009/0093697 A1 | 4/2009 | Mir et al. |
| 2009/0137927 A1 | 5/2009 | Miller |
| 2009/0149730 A1 | 6/2009 | McCrary |
| 2009/0171226 A1 | 7/2009 | Campbell et al. |
| 2009/0178675 A1 | 7/2009 | Turiello |
| 2009/0178676 A1 | 7/2009 | Villax et al. |
| 2009/0194100 A1 | 8/2009 | Minagi |
| 2009/0229605 A1 | 9/2009 | Efrati et al. |
| 2009/0241955 A1 | 10/2009 | Jafari et al. |
| 2009/0241962 A1 | 10/2009 | Jafari et al. |
| 2009/0250061 A1 | 10/2009 | Marasigan |
| 2009/0281481 A1 | 11/2009 | Harding |
| 2009/0308398 A1 | 12/2009 | Ferdinand et al. |
| 2009/0314294 A1 | 12/2009 | Chalvignac |
| 2009/0318851 A1 | 12/2009 | Schenck |
| 2010/0018529 A1 | 1/2010 | Chalvignac |
| 2010/0024819 A1 | 2/2010 | Tiedje |
| 2010/0065057 A1 | 3/2010 | Berthon-Jones |
| 2010/0071696 A1 | 3/2010 | Jafari |
| 2010/0078018 A1 | 4/2010 | Heinonen |
| 2010/0081958 A1 | 4/2010 | She |
| 2010/0101574 A1 | 4/2010 | Bassin |
| 2010/0101576 A1 | 4/2010 | Berthon-Jones |
| 2010/0116276 A1 | 5/2010 | Bayasi |
| 2010/0137737 A1 | 6/2010 | Addington et al. |
| 2010/0147303 A1 | 6/2010 | Jafari et al. |
| 2010/0186741 A1 | 7/2010 | Aylsworth et al. |
| 2010/0218767 A1 | 9/2010 | Jafari et al. |
| 2010/0234758 A1 | 9/2010 | de Menezes |
| 2010/0236553 A1 | 9/2010 | Jafari et al. |
| 2010/0236555 A1 | 9/2010 | Jafari et al. |
| 2010/0252048 A1 | 10/2010 | Young et al. |
| 2010/0258123 A1 | 10/2010 | Somaiya et al. |
| 2010/0262038 A1 | 10/2010 | Tan et al. |
| 2010/0331768 A1 | 12/2010 | Hedmann et al. |
| 2011/0034863 A1 | 2/2011 | Hoffa |
| 2011/0061648 A1 | 3/2011 | Durtschi et al. |
| 2011/0071367 A1 | 3/2011 | Court et al. |
| 2011/0077549 A1 | 3/2011 | Kitai et al. |
| 2011/0100373 A1 | 5/2011 | Efrati et al. |
| 2011/0125052 A1 | 5/2011 | Davenport et al. |
| 2011/0132363 A1 | 6/2011 | Chalvignac |
| 2011/0178427 A1 | 7/2011 | Tan et al. |
| 2011/0196251 A1 | 8/2011 | Jourdain et al. |
| 2011/0201956 A1 | 8/2011 | Alferness et al. |
| 2011/0209702 A1 | 9/2011 | Vuong et al. |

| | | | |
|---|---|---|---|
| 2011/0220112 A1 | 9/2011 | Connor | |
| 2011/0226250 A1 | 9/2011 | LaBollita et al. | |
| 2011/0259330 A1 | 10/2011 | Jafari et al. | |

FOREIGN PATENT DOCUMENTS

| | | | |
|---|---|---|---|
| EP | 0425092 A | 5/1991 | |
| EP | 1270036 | 1/2003 | |
| WO | WO 94/23780 A | 10/1994 | |
| WO | WO 98/06449 A | 2/1998 | |
| WO | WO 00/10634 A | 3/2000 | |
| WO | WO 00/45880 A | 8/2000 | |
| WO | WO 01/74430 A | 10/2001 | |
| WO | WO 02/28460 A | 4/2002 | |
| WO | WO 03/055552 A1 | 7/2003 | |
| WO | WO 04000114 | 12/2003 | |
| WO | WO 2004/084980 A | 10/2004 | |
| WO | WO 2005/105189 | 11/2005 | |
| WO | WO 2006/137784 A1 | 12/2006 | |
| WO | WO 2007145948 | 12/2007 | |
| WO | WO 2009123981 | 10/2009 | |

OTHER PUBLICATIONS

PCT International Search Report and Written Opinion in Application PCT/2009/038810, mailed Jul. 6, 2009, 16 pgs.

PCT International Search Report and Written Opinion in Application PCT/2009/038815, mailed Jul. 1, 2009, 14 pgs.

PCT International Search Report and Written Opinion in Application PCT/US09/038811, mailed Jun. 7, 2009, 13 pgs.

PCT International Search Report and Written Opinion in Application PCT/US2009/038819, mailed Jun. 26, 2009, 12 pgs.

PCT International Search Report and Written Opinion in Application PCT/US2009/038820, mailed Jul. 22, 2009, 14 pgs.

PCT International Search Report and Written Opinion in Application PCT/US201/0026618, mailed Jun. 22, 2010, 19 pgs.

U.S. Appl. No. 12/242,741, Office Action mailed Jan. 10, 2012, 7 pgs.

U.S. Appl. No. 12/334,354, Notice of Allowance mailed Jan. 27, 2012, 7 pgs.

U.S. Appl. No. 12/414,419, Office Action mailed Jan. 20, 2012, 15 pgs.

U.S. Appl. No. 12/242,741, Notice of Allowance mailed Jun. 5, 2012, 5 pgs.

U.S. Appl. No. 12/408,408, Notice of Allowance mailed Jun. 4, 2012, 10 pgs.

U.S. Appl. No. 12/408,414, Office Action mailed Jun. 20, 2012, 9 pgs.

U.S. Appl. No. 12/414,419, Office Action mailed Jul. 18, 2012, 16 pgs.

* cited by examiner

FIG. 4

LEAK-COMPENSATED PRESSURE TRIGGERING IN MEDICAL VENTILATORS

RELATED APPLICATIONS

This application claims the benefit of U.S. Provisional Application No. 61/041,070, filed Mar. 31, 2008, titled "Ventilator Leak Compensation," which application is hereby incorporated by reference.

BACKGROUND

Medical ventilators may determine when a patient takes a breath in order to synchronize the operation of the ventilator with the natural breathing of the patient. In some instances, detection of the onset of inhalation and/or exhalation may be used to trigger one or more actions on the part of the ventilator.

The response performance of a medical ventilator to a patient trigger from the exhalation breath phase into inhalation is an important characteristic of a medical ventilator. A ventilator's trigger response impacts the patient's work of breathing and the overall patient-ventilator synchrony. In patient-initiated ventilation types such as Pressure Support Ventilation (PSV), Proportional Assist Ventilation PAV), etc., the airway pressure drops below the baseline as a patient initiates an inspiratory effort. The ventilator detects the patient's inspiratory effort and uses this information to provide ventilation therapy to the patient.

The trigger response performance of a ventilator is a function of a patient's inspiratory behavior (which includes breathing effort magnitude and timing characteristics) as well as the ventilator's gas delivery dynamics and flow control parameters (actuator response, deadbands, etc.). In conventional pressure triggering modality, the patient effort is detected based on the magnitude of airway pressure drop from the operator-set positive end-expiratory pressure (PEEP). The pressure drop is generated by the patient inspiratory effort as sensed at a patient proximal site in the gas delivery system with no or minimal base flow. The pressure trigger sensitivity is used to determine a phase transition from exhalation into inhalation. In the presence of system leaks, there is a need to provide an adequate base flow to compensate for the leak rate and avoid autocycling (false breath triggering) due to airway pressure drop exceeding the set sensitivity in the absence of patient inspiratory effort.

SUMMARY

This disclosure describes systems and methods for compensating for pressure-dependent elastic sources of leaks in a ventilation system. The disclosure describes a model-based enhancement to conventional pressure triggering methodology that optimizes or attempts to optimize the timing and patient work of pressure triggering performance. The methods and systems may be used with known conventional pressure triggering algorithms (i.e., comparing airway pressure deviation against trigger sensitivity) and in the presence of leak-compensated base flow (to enable PEEP maintenance and avoid autocycling). The methods and systems described herein compensate for the additional effort a patient has to exert to generate the same amount of airway pressure drops compared to no leak condition. That is, under leak conditions, the same patient effort (pressure drop in the lung) would lead to a smaller observable deviation in the pressure at the patient wye/interface or other pressure measurement location, thus the need for increased patient effort to activate a trigger against a set trigger sensitivity.

In part, this disclosure describes a method of compensating for leakage in a ventilation system during delivery of gas from a medical ventilator to a patient. The method includes estimating leakage from the ventilation system during delivery of gas to the patient based on measurements of at least one of pressure and flow. The leakage is modeled as a first leakage component through a first orifice of a fixed size and a second leakage component through a second orifice of a varying size, in which the first and second leakage components are different functions of one or more of instantaneous pressure and instantaneous flow in the ventilation system. The method further includes estimating instantaneous lung flow of gas exhaled or inhaled by the patient during an exhalation phase and identifying a target pressure trigger condition indicative of patient inspiratory effort. The method further includes monitoring an instantaneous pressure at a location in the ventilation system based on one or more measurements of instantaneous pressure or instantaneous flow in ventilation system. The method generates a leak-compensated pressure trigger condition based on the monitored instantaneous pressure, the target pressure trigger threshold set by the operator, the lung flow and combined first and second leakage components. The method then uses the leak-compensated pressure trigger condition to determine when the patient has begun to initiate an inhalation.

This disclosure also describes another method of compensating for leakage in a ventilation system during delivery of gas from a medical ventilator to a patient. The method includes identifying an inelastic leakage in the ventilation system as a first function of at least one of a pressure measurement and a flow measurement in the ventilation system and identifying an elastic leakage in the ventilation system as a second function of at least one of the pressure measurement and the flow measurement in the ventilation system. The method further includes determining that the patient is initiating an inspiration based on the inelastic leakage, the elastic leakage and at least one of the pressure measurement and the flow measurement in the ventilation system.

Yet another aspect of this disclosure describes a pressure support system that includes: a pressure generating system adapted to generate a flow of breathing gas; a ventilation system including a patient interface device; one or more sensors operatively coupled to the pressure generating system or the ventilation system, in which each sensor capable of generating an output indicative of a pressure of the breathing gas; a processor; a leak estimation module that identifies both elastic and rigid orifice sources of leakage in the ventilation system; a compensation module that generates a leak-compensated pressure trigger condition based on the elastic and inelastic sources of leakage and at least one output indicative of a pressure of the breathing gas; and an inspiration detection module that determines when a patient has begun to inhale based on the leak-compensated pressure trigger condition and an output of at least one sensor.

This disclosure further describes a controller for a medical ventilator that includes a microprocessor and a pressure trigger compensation means for adjusting an initial pressure trigger threshold based on instantaneous elastic leakage and instantaneous inelastic leakage of breathing gas from a ventilation system. The pressure trigger compensation means may further include an inelastic leak estimation module that identifies the instantaneous inelastic leakage in the ventilation system and an elastic leak estimation module that identifies the instantaneous elastic leakage in the ventilation system. In another aspect, the pressure trigger compensation means may include a compensation module that generates a leak-compensated pressure trigger condition based on the instantaneous elastic and inelastic leakage and at least one sensor output indicative of a pressure of the breathing gas.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems in which leaks may cause a degradation of performance.

Figure 1:
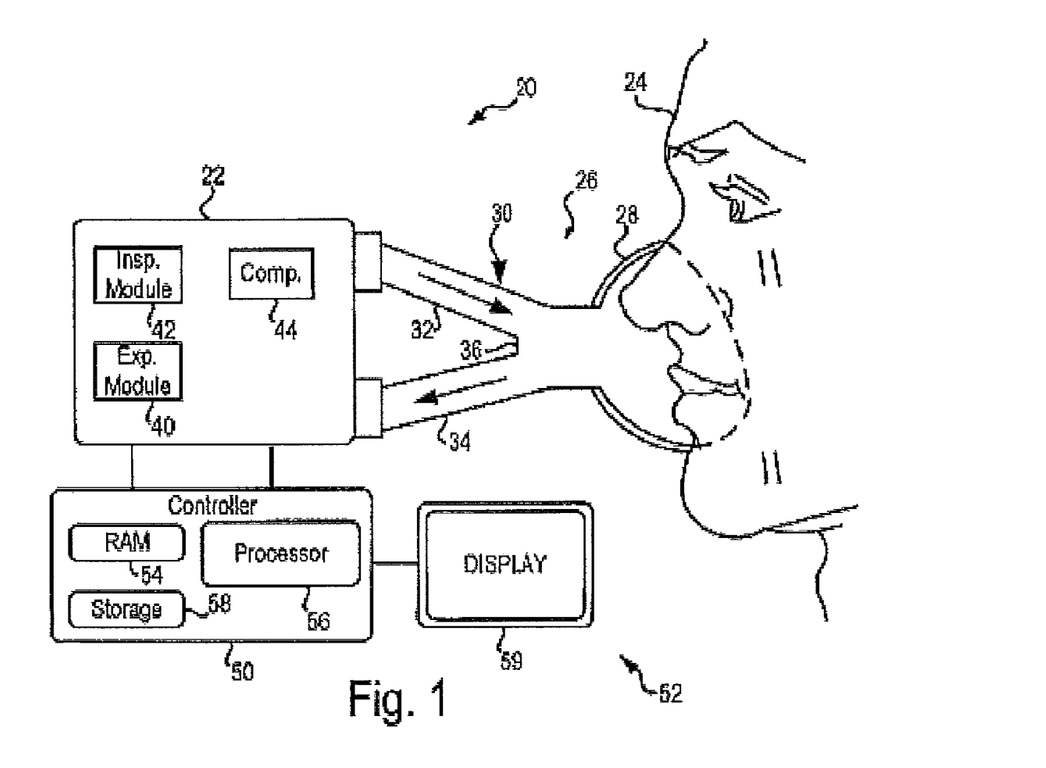
FIG. 1 illustrates an embodiment of a ventilator connected to a human patient.

FIG. 1 illustrates an embodiment of a ventilator 20 connected to a human patient 24. Ventilator 20 includes a pneumatic system 22 (also referred to as a pressure generating system 22) for circulating breathing gases to and from patient 24 via the ventilation tubing system 26, which couples the patient to the pneumatic system via physical patient interface 28 and ventilator circuit 30. Ventilator circuit 30 could be a two-limb or one-limb circuit for carrying gas to and from the patient. In a two-limb embodiment as shown, a wye fitting 36 may be provided as shown to couple the patient interface 28 to the inspiratory limb 32 and the expiratory limb 34 of the circuit 30.

The present systems and methods have proved particularly advantageous in noninvasive settings, such as with facial breathing masks, as those settings typically are more susceptible to leaks. However, leaks do occur in a variety of settings, and the present description contemplates that the patient interface may be invasive or non-invasive, and of any configuration suitable for communicating a flow of breathing gas from the patient circuit to an airway of the patient. Examples of suitable patient interface devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. Compressor 44 or another source(s) of pressurized gas (e.g., air and oxygen) is coupled with inspiratory module 42 to provide a gas source for ventilatory support via inspiratory limb 32.

The pneumatic system may include a variety of other components, including sources for pressurized air and/or oxygen, mixing modules, valves, sensors, tubing, accumulators, filters, etc. Controller 50 is operatively coupled with pneumatic system 22, signal measurement and acquisition systems, and an operator interface 52 may be provided to enable an operator to interact with the ventilator (e.g., change ventilator settings, select operational modes, view monitored parameters, etc.). Controller 50 may include memory 54, one or more processors 56, storage 58, and/or other components of the type commonly found in command and control computing devices.

The memory 54 is computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 56. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 50 issues commands to pneumatic system 22 in order to control the breathing assistance provided to the patient by the ventilator. The specific commands may be based on inputs received from patient 24, pneumatic system 22 and sensors, operator interface 52 and/or other components of the ventilator. In the depicted example, operator interface includes a display 59 that is touch-sensitive, enabling the display to serve both as an input and output device.

Figure 2:
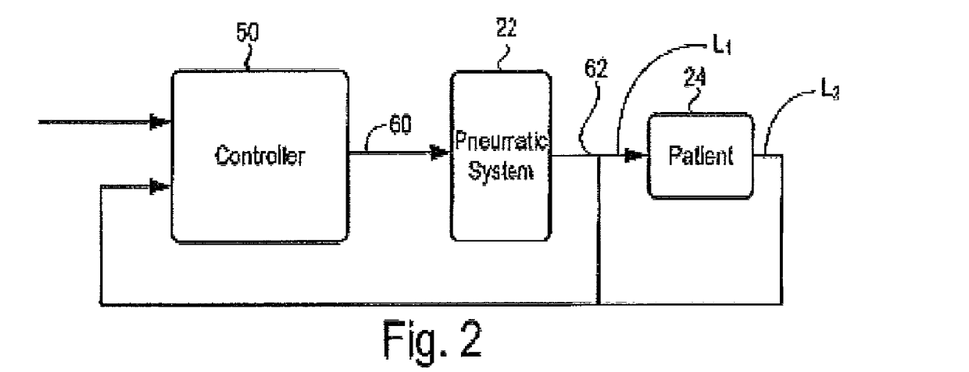
FIG. 2 schematically depicts exemplary systems and methods of ventilator control.

FIG. 2 schematically depicts exemplary systems and methods of ventilator control. As shown, controller 50 issues control commands 60 to drive pneumatic system 22 and thereby circulate breathing gas to and from patient 24. The depicted schematic interaction between pneumatic system 22 and patient 24 may be viewed in terms of pressure and/or flow "signals." For example, signal 62 may be an increased pressure which is applied to the patient via inspiratory limb 32.

Control commands 60 are based upon inputs received at controller 50 which may include, among other things, inputs from operator interface 52, and feedback from pneumatic system 22 (e.g., from pressure/flow sensors) and/or sensed from patient 24.

In many cases, it may be desirable to establish a baseline pressure and/or flow trajectory for a given respiratory therapy session. The volume of breathing gas delivered to the patient's lung ($L_1$) and the volume of the gas exhaled by the patient ($L_2$) are measured or determined, and the measured or predicted/estimated leaks are accounted for to ensure accurate delivery and data reporting and monitoring. Accordingly, the more accurate the leak estimation, the better the baseline calculation of delivered and exhaled volume as well as event detection (triggering and cycling phase transitions).

When modeling the delivery of gas to and from a patient 24 via a closed-circuit ventilator, one simple assumption is that compliance of the ventilator circuit 30 is fixed and that all gas injected into the ventilator circuit 30 that does not exit the circuit 30 via the expiratory limb 34 fills the circuit as well as the patient's lungs and causes an increase in pressure. As gas is injected ($L_1$), the lung responds to the increased gas pressure in the circuit 30 by expanding. The amount the lung expands is proportional to the lung compliance and is modeled as a function of gas pressure differential (Compliance=volume delivered/pressure difference).

The term circuit compliance is used to refer to the amount the pressure in the ventilator circuit 30 (or ventilator circuit 30 and attached patient interface 28, depending on how the compliance is determined) changes based on changes in volume delivered into the circuit. In an embodiment, the circuit compliance may be estimated by pressurizing the ventilator circuit 30 (or circuit 30 and interface 28 combination) when flow to the patient is blocked and measuring the volume of additional gas introduced to cause the pressure change (compliance=volume delivered/pressure difference).

The term circuit resistance is used to refer to the amount the pressure changes between two sites upstream and downstream the ventilator circuit as a function of volumetric flow rate through that circuit. Tubing resistance may be modeled as a two-parameter function of flow:

$$\text{Pressure difference} = K_1 * \text{Flow} + K_2 * \text{Flow}^2 = \text{Flow} * (K_1 + K_2 * \text{Flow})$$

In which $K_1$ and $K_2$ are empirically derived constants. For example) in an embodiment, the circuit resistance may be estimated by passing several fixed flow rates through the circuit and measuring the pressure difference between certain upstream and downstream sites and finding the best curve fit to the collected data.

Such a method of determining compliance and resistance may be executed by the operator prior to attaching the patient to the ventilator as part of the set up of the ventilator 20 to provide therapy. Other methods of determining compliance and/or resistance are also possible and could be adapted for use with the disclosed leak-compensation systems and methods described herein.

Errors may be introduced due to leaks in the ventilation tubing system 26. The term ventilation tubing system 26 is used herein to describe the ventilator circuit 30, any equipment attached to or used in the ventilator circuit 30 such as water traps, monitors, drug delivery devices, etc. (not shown), and the patient interface 28. Depending on the embodiment, this may include some equipment contained in the inspiration module 42 and/or the expiration module 40. When referring to leaks in or from the ventilation tubing system 26, such leaks include leaks within the tubing system 26 and leaks where the tubing system 26 connects to the pressure generator 22 or the patient 24. Thus, leaks from the ventilation tubing system 26 include leaks from the ventilator circuit 30, leaks from the patient interface 28 (e.g., masks are often provided with holes or other pressure relief devices through which some leakage may occur), leaks from the point of connection of the patient interface 28 to the patient 24 (e.g., leaks around the edges of a mask due to a poor fit or patient movement), and leaks from the point of connection of the patient interface 28 to the circuit 30 (e.g., due to a poor connection between the patient interface 28 and the circuit 30).

For the purpose of estimating how a leak flow rate changes based on changes in pressure in the ventilation tubing system 26, the instantaneous leak may be modeled as a leak through a single orifice or opening of a fixed size in which that size is determined based on comparing the total volume into the inspiratory limb 32 and out of the expiratory limb 34. However, this leak model does not take into account any elastic component of leak source(s) in the system 26, that is how much any of the holes or openings in the ventilation tubing system 26 through which leakage occurs may change due to an increase or decrease in pressure.

It has been determined that not accounting for elastic leakage from the ventilation tubing system 26 can cause many problems. First, if only the inelastic/fixed orifice model is used to estimate leak, the subsequent errors caused by ignoring the elastic effects of any actual leaks end up generating inaccurate estimates of flow rates into the lung. This can cause the ventilator 20 to estimate gas volume delivered into the lung inaccurately when, in fact, the elastic leaks in the system 26 have let more gas escape than estimated. Second, if the elasticity of the leak source is ignored, any other calculation, estimate, or action that the ventilator 20 may perform which is affected by the leak estimate will be less accurate.

In the systems and methods described herein, the pressure triggering mechanism of a ventilator from an exhalation phase into an inhalation phase is made more accurate by compensating the pressure trigger to account for both the fixed (rigid) and elastic components of the system leakage. This results in a more accurate and timely triggering into the inhalation cycle of the ventilator 20 and is beneficial to the patient 24 as it requires the patient 24 to exert less effort to initiate the inhalation cycle. While the systems and methods are presented in the context of a pressure triggering mechanism deployed during the exhalation cycle of the ventilator, the technology described herein could be used to compensate for leakage when using any type of pressure-based mechanisms derived from patient respiratory effort to trigger an event in a ventilator.

Figure 3:
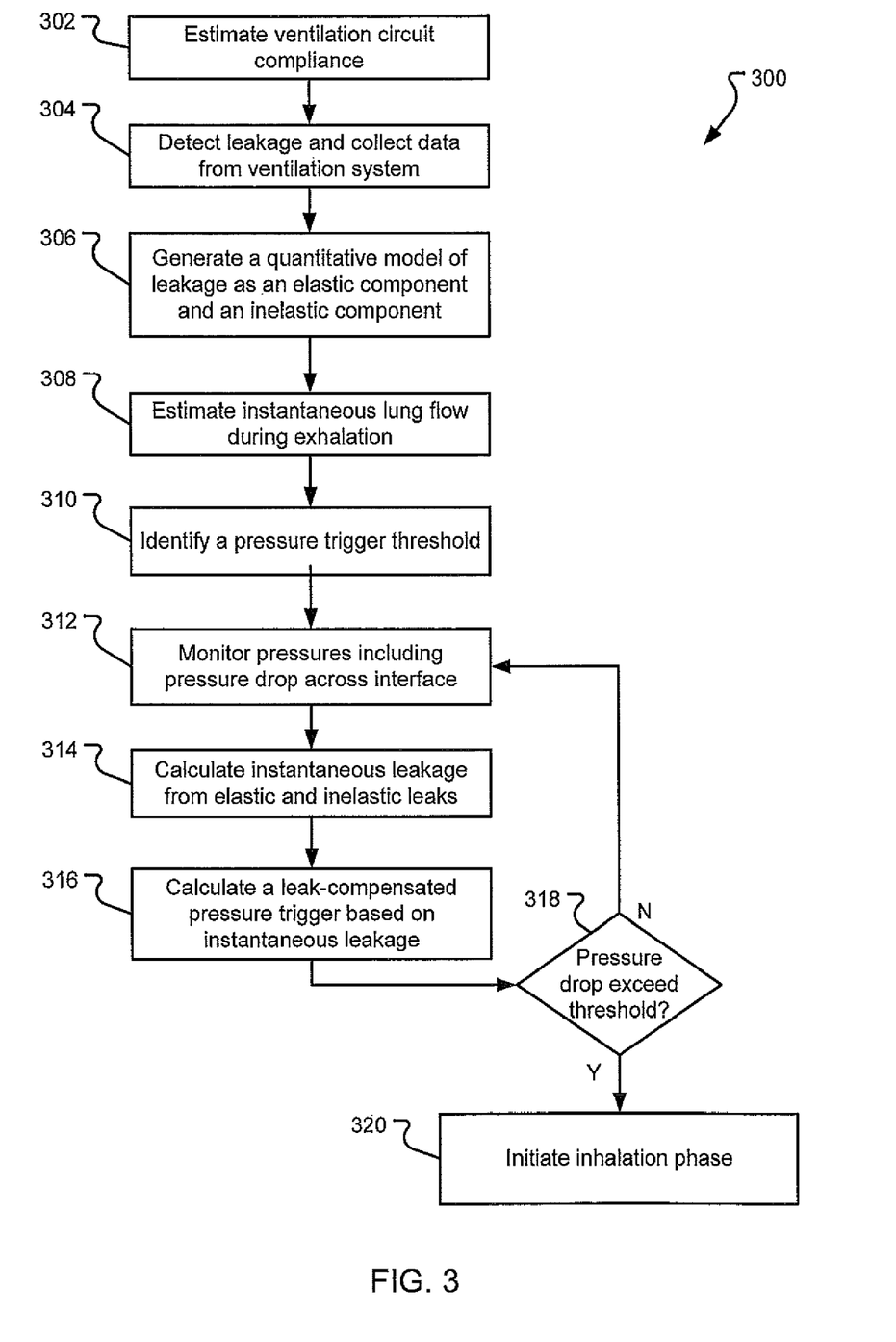
FIG. 3 illustrates an embodiment of a method of compensating for leakage in a ventilation system during delivery of gas from a medical ventilator to a patient.

FIG. 3 illustrates an embodiment of a method of compensating for leakage in a ventilation system during delivery of gas from a medical ventilator to a patient. In the method 300 shown, a medical ventilator such as that described above with reference to FIGS. 1 and 2 is used to provide ventilation to a patient.

In the method 300 illustrated, the ventilator circuit compliance and resistance may be estimated in a compliance/resistance estimation operation 302. In an embodiment, this is usually performed prior to connecting the ventilator to the patient (as previously described).

In the method 300 illustrated, the ventilator is connected to the patient and operated for some period of time, e.g., for a breath, and data is obtained in a data collection operation 304. While the data collection operation 304 may be performed prior to connection to the patient, it is also anticipated that the operation should be performed while the patient is receiving therapy from the ventilator so that leaks from the connection of the ventilation system to the patient may be characterized as well as the other leaks in the system. In an embodiment the data collection operation 304 includes operating the ventilator for a period of time and collecting measurements of pressure and/or flow in ventilation system.

The data obtained in the data collection operation 304 is then used to quantify the parameters of the leak model in the parameter quantification operation 306. In an embodiment, the parameter quantification operation 306 uses the data obtained in the data collection operation 304, e.g., the total leak volume during one breath cycle (inhalation and exhalation) and some or all of the pressure and flow data collected during the data collection operation 304. The data may be applied to a preselected mathematical formula in order to solve for parameters in the formula. In an embodiment, the mathematical formula is a leakage model that separates the leak into the sum of two leak components, inelastic leak and elastic leak, in which each component represents a different relationship between the quantity of leakage from the ventilation system and the measured current/instantaneous pressure and/or flow of gas in the ventilation system. As discussed above, the inelastic leak may be modeled as the flow through a rigid orifice of a fixed size while the elastic leak may be modeled as the flow through a different orifice of a size that changes based on the pressure (or flow) of the gas in the ventilation system.

An example of a method and system for modeling leak in a ventilation system as a combination of an elastic leak component and an inelastic leak component can be found in commonly-assigned U.S. Provisional Patent Application Ser. No. 61/041,070, filed Mar. 31, 2008, titled VENTILATOR LEAK COMPENSATION, which application is hereby incorporated by reference herein. The VENTILATOR LEAK COMPENSATION represents one way of characterizing the leak from a ventilation system as a combination of elastic and inelastic components. Other methods and models are also possible and may be adapted for use with this technology.

In an embodiment, the result of the parameter quantification operation 306 is a quantitative mathematical model, equation or set of equations of leak that, from one or more measurements of pressure and/or flow in the ventilation system, can be used to calculate an estimate of the resulting leak from the ventilation system. Thus, given the mathematical model, pressure and/or flow data can be monitored during therapy and the instantaneous and total leak from the ventilation system can be calculated. The resulting leak value will take into account both elastic leak and the inelastic leak.

In an embodiment, the data collection operation 304 and the parameter quantification operation 306 may be performed as a single operation or as separate operations. In an embodiment, the operations 304 and 306 may be repeated periodically, based on time or breathing cycles, in order to obtain accurate estimates. Furthermore, the accuracy of the parameters of the leakage model may be periodically checked.

For example, in an embodiment, the data collection operation 304 may calculate or estimate the total leak volume for a particular breath of a patient. This estimate may then be used in the parameter quantification operation 306 to generate the leak model for use in calculating the instantaneous leak in a subsequent breath. In an embodiment, the data collection operation 304 and the parameter quantification operation 306 are repeated at the end of each breath so that the instantaneous leak is estimated using a model derived from data taken during the immediately previous breath.

In the embodiment shown, the ventilator begins monitoring for patient-initiated triggering (i.e., transition from exhalation into inhalation) as illustrated by operation 308. This operation 308 may be ongoing or may only occur after a determination that the ventilator has cycled into the exhalation phase of the respiration. In yet another embodiment, there may be a restricted period at the beginning of the exhalation phase during which no transitions are allowed (to ensure a minimum period of exhalation). During the restricted period, the phase detection algorithm for triggering may or may not be executed.

When monitoring for patient-initiated triggering, the system obtains current measurements from sensors located at specific sites in the ventilation pathway in an obtain measurements operation 310. The obtain measurements operation 310 may include obtaining pressure and/or flow measurements from one or more locations within the ventilation system. Depending upon how a particular leak model and the triggering criteria are defined, the operation 310 may also include making one or more calculations using the measurements. For example, a pressure trigger may be characterized as a pressure drop observed at the patient interface while the ventilation system may not have a pressure sensor at that location in the ventilation system. Thus, data from a sensor or sensors located elsewhere in the system may be mathematically manipulated in order to obtain an estimate of the pressure drop observed at the patient interface in order to compare the current observed pressure drop to the putative pressure drop caused by the same magnitude of the patient's inspiratory effort under no leak condition.

In the method 300, after the current measurements have been obtained in operation 310, the current leak for the sampling period is calculated in an instantaneous leak calculation operation 312. The operation 312 uses the mathematical model of the leak including the parameters determined in the parameter quantification operation 306 and the current pressure and/or flow measurements to generate an instantaneous leakage value from the ventilation system. As the model characterizes both the elastic and inelastic leak components, the calculated leak represents the total leak due to the combination of both leak components.

The term instantaneous is used herein to describe a determination made for any particular instant or sampling period based on the measured data for that instant. For example, if a pressure measurement is taken every 5 milliseconds (sample period), the pressure measurement and the leak model can be used to determine an instantaneous leak flow rate based on the pressure measurement. With knowledge of the length of the sample period, the instantaneous flow rate may then be used to determine an instantaneous volume of gas flowing through a part of the circuit during that sample period. For longer periods covering multiple sampling periods the instantaneous values for each sampling period may be integrated to obtain a total volume. If a measurement is also the most recent measurement taken, then the instantaneous value may also be referred to as the current value.

After the current leak has been calculated, the method 300 further estimates the instantaneous lung flow to or from the patient in a lung flow estimation operation 314. The estimated lung flow is compensated for the leak calculated in the instantaneous leak calculation operation 312.

In the embodiment shown, the instantaneous lung flow information is used in a pressure trigger identification operation 315 to identify a pressure trigger into inhalation. The pressure trigger sensitivity is a threshold set by the operator to indicate when sufficient airway pressure drop has been generated by the patient during the exhalation phase to allow a transition into a new inhalation phase. In the absence of any leak, as discussed in greater detail below, when the ventilator detects an occurrence of the pressure drop equal to or in excess of the pressure trigger, the ventilator will treat this condition as indicating that the patient has begun to inhale. Thus, the pressure trigger represents a leak-free pressure deviation caused by the patient's inspiratory effort that the ventilator actively monitors for. In an embodiment, the pressure trigger threshold may be received by the ventilator from the operator upon the initial setup of the ventilator to provide therapy to the patient or may be received (changed) during therapy.

A leak-compensation operation 316 is then performed in which the airway pressure trigger mechanism is compensated for the elastic and inelastic leaks calculated in instantaneous leak calculation operation 314. This operation 316 modifies the estimated or measured patient airway pressure to account for the elastic and inelastic leaks in the system (i.e., compute estimated pressure drop caused by the same magnitude of patient inspiratory effort if there was no leak). For example, in an embodiment, the leak-compensation operation 316 may include calculating the amount of instantaneous leak and adjusted pressure drop (i.e., estimate the would-be pressure drop if there were no leak). This may then be used to either adjust the no-leak pressure trigger threshold or compute a corresponding (putative) no-leak pressure deviation that would have been generated by the same magnitude of patient effort. The resulting leak-compensated trigger condition, i.e., adjusted sensitivity or no-leak pressure deviation, may be used to check trigger criteria for a new inspiration. Under conventional pressure triggering modality, there is no base flow delivered by the ventilator during exhalation. Therefore, in the absence of any leaks, when the patient initiates an inspiratory effort by generating a negative pressure in the lung, the pressure measured at the patient-wye is close to the lung pressure and may serve as a good indicator of the force exerted by the inspiratory muscles. In the presence of leaks, there is a need for adequate amount of base flow to be delivered by the ventilator to maintain a set PEEP level during the exhalation phase. So, when the patient initiates an inspiratory effort by generating a negative pressure in the lung, the pressure measured at the patient-wye would be observed to be higher than the pressure in the lung because of the pressure difference due to the flow going into the lung and airway resistance (e.g., Pressure drop resistance*flow, or pressure drop=flow*[$K_1$+$K_2$*flow]). In an embodiment, the compensation may be of a simple algebraic nature such as reducing the pressure triggering threshold (sensitivity) in accordance with the leak-induced airway pressure drop to account for the amount of pressure generated by the patient which is unobserved at the circuit wye because of availability of a flow source (ventilator base flow and/or flow through the leak orifice). Such a compensation effectively reduces the value of the pressure trigger threshold to a lower, more sensitive threshold based on the current pressure and/or flow measurements and the calculated elastic and inelastic components of the system leakage. In another embodiment, the compensation may include augmentation of the circuit-wye pressure drop by the pressure difference due to the generated lung flow (derived from ventilator base flow and/or through the leak source) under leak condition. The augmented pressure drop may then be compared against the set pressure trigger threshold (sensitivity) to check for initiation of a new inhalation.

The ventilator then uses the leak-compensated pressure trigger condition in a determination operation 318 that compares the current measurement(s) of pressure and/or flow to the pressure trigger condition to determine if the condition is met and, therefore, that inhalation has begun. If the determination operation 318 determines that the leak-compensated inhalation pressure trigger condition has not been exceeded, inhalation has not begun and the method 300 waits until the next sampling point (as illustrated by the waiting operation 322) and then repeats the measurement collection operation 310 so that the analysis may continue to be performed on the next set of measurements.

If the determination operation 318 determines that the trigger has been reached, then the ventilator considers inhalation to have been initiated by the patient as indicated by the inhalation operation 320. Depending on the therapy type and design of the ventilator, the inhalation operation 320 may include the triggering of an inhalation cycle in which pressure or flow is changed to follow a desired trajectory. Other actions may also be performed upon detection of inspiration such as the logging of different or additional data, and the opening and/or closing of valves in the ventilation system to modify the flow path of gas.

Although not shown, in an embodiment after inhalation has been deemed detected by the method 300, some or all of the method 300 may be repeated for the next breathing cycle. For example, upon further detection of the end of the exhalation cycle of the patient (i.e., detection of next inhalation by the patient) the leak estimation operation 304 and the parameter quantification operation 306 may be repeated to calculate a revised leak model based on the most recent data. This revised model may then be used to identify the next phase transition initiated by the patient.

In another embodiment, the lung flow estimation operation 314 may be performed for a certain interval or performed continuously during therapy. This lung flow may be estimated based on characteristics derived from a single sample period, a single breath or based on a representative parameter derived from an ensemble of several breaths.

The pressure trigger threshold may be revised after each new estimation of the lung flow until the start of a new inhalation phase is established. In yet another embodiment, the operator may be allowed to disable leak compensation of the pressure trigger threshold.

Figure 4:
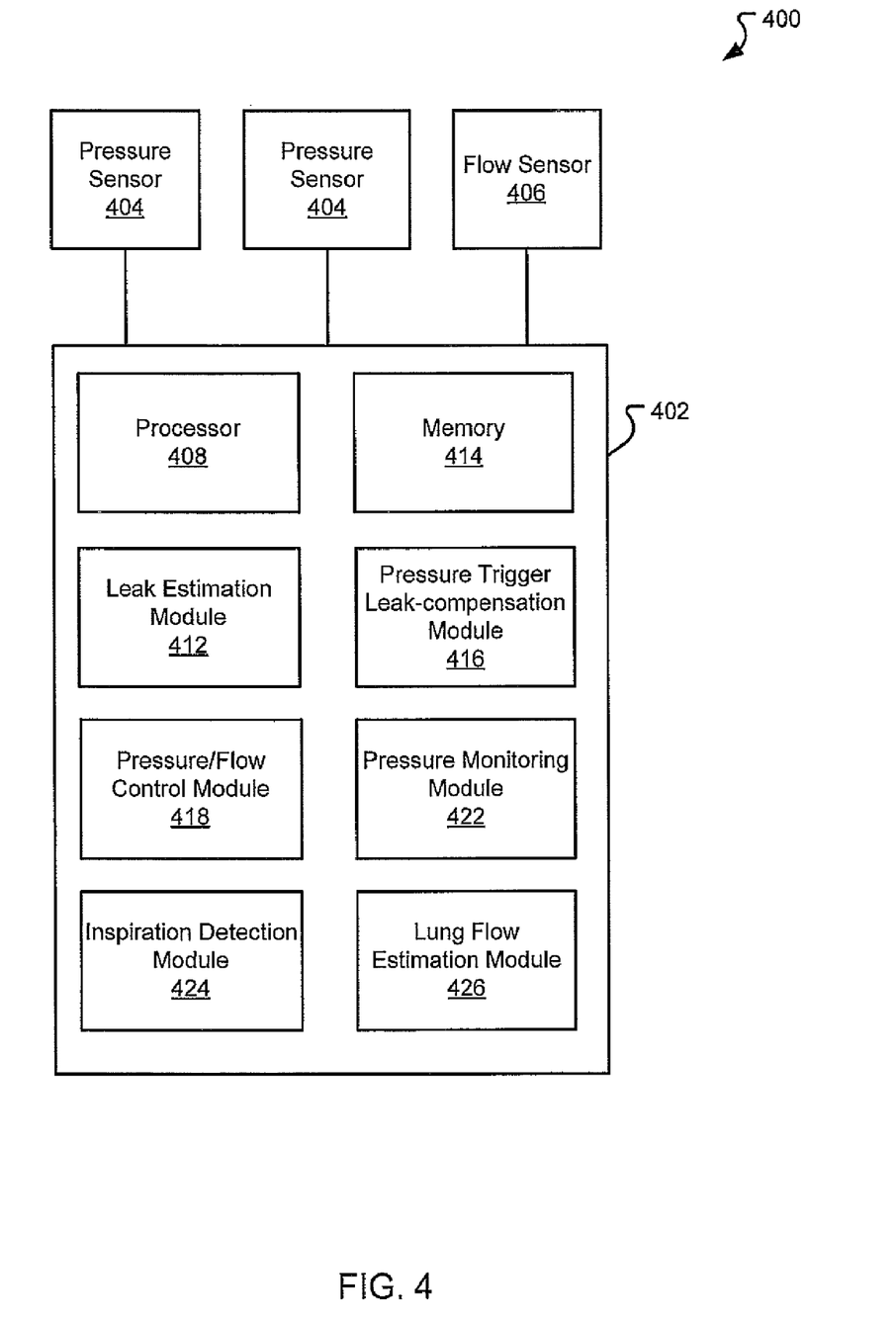
FIG. 4 illustrates a functional block diagram of modules and other components that may be used in an embodiment of ventilator that compensates for leaks.

FIG. 4 illustrates a functional block diagram of modules and other components that may be used in an embodiment of ventilator that compensates for leaks. In the embodiment shown, the ventilator 400 includes pressure sensors 404 (two are shown placed at different locations in the ventilator-patient system), flow sensors (one is shown), and a ventilator control system 402. The ventilator control system 402 controls the operation of the ventilator and includes a plurality of modules described by their function. In the embodiment shown, the ventilator control system 402 includes a processor 408, memory 414 which may include mass storage as described above, a leak estimation module 412 incorporating a parametric leak model accounting for both elastic and rigid orifice leak sources such as that described in U.S. Provisional Application 61/041,070 previously incorporated herein, a pressure trigger leak-compensation module 416, a pressure and flow control module 418, a monitoring module 422, an inhalation detection module 424, and a lung flow estimation module 426. The processor 408 and memory 414 have been discussed above. Each of the other modules will be discussed in turn below.

The main functions of the ventilator such as receiving and interpreting operator inputs and changing pressure and flow of gas in the ventilator circuit are performed by the control module 418. In the context of the methods and systems described herein, the module 418 will perform one or more actions upon the determination that a patient receiving therapy is inhaling and exhaling. The determination of patient-initiated inspiration is made by the inhalation detection module 424 which passes the determination on to the control module 418 when it occurs.

In an embodiment, the inhalation detection module 424 uses a leak-compensated pressure trigger threshold or adjusted proximal pressure drop (generically referred to as the leak-compensated trigger condition) to determine when inhalation is being initiated by the patient. The conditions of the ventilation system, such as pressure and/or flow, are monitored using the sensors 404, 406 and the conditions are processed and used by the leak-compensated pressure trigger module. When it is determined that the conditions indicate that the triggering criteria have been met, e.g., by continuously or periodically comparing the current proximal pressure to the leak-compensated pressure trigger threshold, inhalation may be deemed to have been initiated.

In an embodiment, a backup leak-compensated flow triggering mechanism may be incorporated as a precautionary measure to build redundancy for safety reasons. The sensitivity of the backup flow trigger may be fixed or set by the operator. The estimated instantaneous leak-compensated lung flow may be compared against the flow trigger sensitivity (threshold) to determine if an inspiratory event has occurred.

The current conditions in the ventilation system are monitored by the monitoring module 422. This module 422 collects the data generated by the sensors 404, 406 and may also perform certain calculations on the data to make the data more readily usable by other modules or may process the current data and/or previously acquired data or operator input to derive auxiliary parameters or attributes of interest. In an embodiment, the monitoring module 422 receives data and provides it to each of the other modules in the ventilator control system 402 that need the current pressure or flow data for the system.

The leak-compensated pressure trigger test is preformed by the pressure trigger leak-compensation module 416. The pressure trigger leak-compensation module 416 calculates the leak-compensated pressure trigger threshold using the estimated or measured lung flow and the airway characteristics (e.g., resistance of the pathway to gas flow. Pressure drop=lung flow*F[$C_1$+$C_2$*lung flow], $C_1$ and $C_2$ may be assumed constant or estimated periodically) to account for the pressure drop across the airway to the lung and thus obtain an estimate of the actual pressure drop in the lung caused by the patient's inspiratory effort. This derived airway pressure drop may be subtracted from the proximal pressure measured at the circuit-wye to be compared against the pressure sensitivity threshold set by the operator. Alternatively, the derived airway pressure drop may be subtracted from the set threshold to be used for testing the measured circuit-wye pressure to determine occurrence of an inspiratory trigger. For lung flow estimation, the calculated total instantaneous leak (sum of elastic Leak and inelastic leak provided by the leak estimation module 412), gas flows delivered by the ventilator, flow rate leaving the ventilator, and flow compression in the circuit may be used. Circuit tubing and airway properties (resistance, compliance, inductance, etc.) are either measured prior to patient setup, or given by the operator, or may be derived on an ongoing basis when deemed required.

In the embodiment shown, the compensated inhalation pressure trigger condition is calculated by the information provided by the lung flow module 426. The lung flow module 426 uses a quantitative model for lung flow of the patient during exhalation and from this characterization and pressure and flow measurements generates an estimate for instantaneous lung flow.

The leak model is generated by the leak estimation module 412 which creates one or more quantitative mathematical models, equations or correlations that uses pressure and flow observed in the ventilation system over regular periods of respiratory cycles (inhalation and exhalation) and apply physical and mathematical principles derived from mass balance and characteristic waveform settings of ventilation modalities (regulated pressure or flow trajectories) to derive the parameters of the leak model incorporating both rigid and elastic (variable pressure-dependent) orifices. In an embodiment, the mathematical model may be a model such as:

$$Q_{inelastic} = R_1 * P_i^x$$

$$Q_{elastic} = R_2 * P_i^y$$

wherein $Q_{elastic}$ is the instantaneous leak flow due to elastic leaks in the ventilation system, $Q_{inelastic}$ is the instantaneous leak flow due to inelastic leaks in the ventilation system, $R_1$ is the inelastic leak constant, $R_2$ is the elastic leak constant, $P_i$ is the current or instantaneous pressure measurement, x is an exponent for use when determining the inelastic leak and y is an exponent different than x for use when determining the elastic leak. The group $R_1*P_i^x$ represents flow through an orifice of fixed size as a function of instantaneous pressure $P_i$ and the group $R_2*P_i^y$ represents flow through a different orifice that varies in size based on the instantaneous pressure. The equations above presuppose that there will always be an elastic component and an inelastic component of leakage from the ventilation system. In the absence of an elastic component or a leak source of varying size, $R_2$ would turn out be zero.

In the embodiment shown, the current or instantaneous elastic leak is calculated by the leak estimation module 412. The calculation is made using the elastic leak portion of the leak model developed by the leak estimation module 412 and the pressure data obtained by the monitoring module 422. The leak estimation module 412 may calculate a new instantaneous elastic leak flow or volume for each pressure sample taken (i.e., for each sampling period) by the monitoring module 422. The calculated elastic leak may then be provided to any other module as needed.

In the embodiment shown, the current or instantaneous inelastic leak is also calculated by the leak estimation module 412. The calculation is made using the inelastic leak portion of the leak model and the pressure data obtained by the monitoring module 422. The leak estimation module 412 may calculate a new instantaneous inelastic leak flow or volume for each pressure sample taken (i.e., for each sampling period) by the monitoring module 422. The calculated inelastic leak may then be provided to any other module as needed.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. For example, the operations and steps of the embodiments of methods described herein may be combined or the sequence of the operations may be changed while still achieving the goals of the technology. In addition, specific functions and/or actions may also be allocated in such as a way as to be performed by a different module or method step without deviating from the overall disclosure. In other words, functional elements being performed by a single or multiple components, in various combinations of hardware and software, and individual functions can be distributed among software applications. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the present invention. For example, the systems and methods described herein could be adapted for more accurately determining the onset of inhalation or of coughing events. Numerous other changes may be made which will readily suggest themselves to those skilled in the art and which are encompassed in the spirit of the disclosure and as defined in the appended claims.

What is claimed is:

1. A method of compensating for leakage in a ventilation system during delivery of gas from a medical ventilator to a patient comprising:
   estimating leakage from the ventilation system during delivery of gas to the patient based on measurements of at least one of pressure and flow;
   modeling the leakage as a first leakage component through a first orifice of a fixed size and a second leakage component through a second orifice of a varying size, wherein the first and second leakage components are different functions of one or more of instantaneous pressure and instantaneous flow in the ventilation system;
   estimating instantaneous lung flow of gas exhaled or inhaled by the patient during an exhalation phase;
   identifying a target pressure trigger threshold indicative of patient inspiratory effort;
   monitoring an instantaneous pressure at a location in the ventilation system based on one or more measurements of instantaneous pressure or instantaneous flow in the ventilation system;
   generating a leak-compensated pressure trigger condition based on the monitored instantaneous pressure, the target pressure trigger threshold, the estimated instantaneous lung flow and the second leakage component; and
   using the leak-compensated pressure trigger condition to determine when the patient has begun to initiate an inhalation.

2. The method of claim 1 wherein using comprises:
   triggering an inhalation cycle of the medical ventilator based on the leak-compensated pressure trigger condition.

3. The method of claim 1 wherein monitoring the instantaneous pressure further comprises:
   generating an estimate of the instantaneous pressure drop at a patient interface based on one or more measurements taken at a different location in the ventilation system.

4. The method of claim 1 further comprising:
   generating the leak-compensated pressure trigger condition based on the estimated instantaneous lung flow, the monitored instantaneous pressure, the target pressure trigger threshold, the second leakage component and the first leakage component.

5. The method of claim 1 further comprising:
   in a subsequent breath, repeating one or more of the operations of claim 1 to generate a revised leak-compensated pressure trigger condition.

6. The method of claim 1 further comprising:
   estimating leakage from the ventilation system during delivery of gas to the patient based on measurements of at least one of pressure and flow taken from a previous breath.

7. The method of claim 1 further comprising:
   estimating leakage from the ventilation system during delivery of gas to the patient based on measurements of at least one of pressure and flow taken over a plurality of previous breaths.

8. The method of claim 1 further comprising:
   estimating an attribute indicative of compliance or resistance of the ventilation system; and
   generating the leak-compensated pressure trigger condition based on the estimated instantaneous lung flow, the monitored instantaneous pressure, the target pressure trigger threshold, the second leakage component and the attribute of the ventilation system.

9. The method of claim 1 wherein the target pressure trigger threshold indicative of patient inspiratory effort is estimated based on the estimated instantaneous lung flow of gas inhaled by the patient.

10. A method of compensating for leakage in a ventilation system during delivery of gas from a medical ventilator to a patient comprising:
    identifying an inelastic leakage in the ventilation system as a first function of at least one of a pressure measurement and a flow measurement in the ventilation system;
    identifying an elastic leakage in the ventilation system as a second function of at least one of the pressure measurement and the flow measurement in the ventilation system; and
    determining that the patient is initiating an inspiration based on the inelastic leakage, the elastic leakage and the at least one of the pressure measurement and the flow measurement in the ventilation system.

11. The method of claim 10 further comprising:
    identifying an initial pressure trigger threshold for use when there is no leakage in the ventilation system; and
    generating a leak-compensated pressure trigger condition based on the initial pressure trigger threshold, the inelastic leakage, the elastic leakage and at least one of the pressure measurement and the flow measurement in the ventilation system.

12. The method of claim 10 wherein determining that the patient is initiating an inspiration comprises:
    monitoring the pressure measurement in the ventilation system; and
    comparing the pressure measurement to the leak-compensated pressure trigger condition.

13. The method of claim 12 further comprising:
    based on the comparing operation, triggering an action by the medical ventilator.

14. The method of claim 13 wherein the action is initiating an inhalation cycle.

15. The method of claim 11 wherein identifying the leak-compensated pressure trigger condition comprises:
    estimating instantaneous lung flow of gas inhaled by the patient during system exhalation phase; and
    calculating the leak-compensated pressure trigger condition based on the estimated instantaneous lung flow.

16. The method of claim 10 wherein determining that the patient is initiating an inspiration further comprises:
    calculating a leak-compensated pressure trigger condition based on the inelastic leakage, the elastic leakage and the pressure measurement in the ventilation system; and
    comparing the leak-compensated pressure trigger condition to the pressure measurement in the ventilation system.

17. The method of claim 16 further comprising:

upon receipt of a pressure measurement, calculating an instantaneous inelastic leakage and an instantaneous elastic leakage based on a received pressure measurement; and recalculating the leak-compensated pressure trigger condition based on the instantaneous inelastic leakage, the instantaneous elastic leakage and the received pressure measurement.

18. A pressure support system comprising:

a pressure generating system adapted to generate a flow of breathing gas;

a ventilation system including a patient interface device;

one or more sensors operatively coupled to the pressure generating system or the ventilation system, each sensor capable of generating an output indicative of a pressure of the breathing gas;

a processor;

an elastic leak estimation module that identifies an elastic leakage in the ventilation system;

a compensation module that generates a leak-compensated pressure trigger condition based on the elastic leakage and at least one output indicative of a pressure of the breathing gas; and an inspiration detection module that determines when a patient has begun to inhale based on the leak-compensated pressure trigger condition and an output of at least one sensor.

19. The system of claim 18 further comprising:

an inelastic leak estimation module that identifies an inelastic leakage in the ventilation system; and wherein the compensation module further generates the leak-compensated pressure trigger condition based on the inelastic leakage.

20. The system of claim 19 further comprising:

a pressure monitoring module that monitors at least one output of the one or more sensors and provides data indicative of the pressure of the breathing gas to the elastic leak estimation module.

21. A controller for a medical ventilator comprising:

a microprocessor; and a pressure trigger compensation means for adjusting an initial pressure trigger threshold, based on:

identifying an elastic leakage in a ventilation system as a first function of at least one of a pressure measurement and a flow measurement in the ventilation system;

identifying an inelastic leakage in the ventilation system as a second function of at least one of the pressure measurement and the flow measurement in the ventilation system; and generating a leak-compensated pressure trigger condition based on the initial pressure trigger threshold, the inelastic leakage, the elastic leakage and at least one of the pressure measurement and the flow measurement in the ventilation system.

22. The controller of claim 21 wherein the pressure trigger compensation means further comprises:

an inelastic leak estimation module that identifies the instantaneous inelastic leakage in the ventilation system; and an elastic leak estimation module that identifies the instantaneous elastic leakage in the ventilation system.

23. The controller of claim 21 wherein the pressure trigger compensation means comprises:

a compensation module that generates the leak-compensated pressure trigger condition based on the instantaneous elastic leakage and at least one sensor output indicative of the pressure measurement in the ventilation system.

* * * * *